United States Patent
Hunter et al.

(10) Patent No.: US 9,062,120 B2
(45) Date of Patent: Jun. 23, 2015

(54) BINDING PROTEINS HAVING TETHERED LIGHT CHAINS

(71) Applicants: Michael Hunter, San Diego, CA (US); Ronald Swanson, San Diego, CA (US)

(72) Inventors: Michael Hunter, San Diego, CA (US); Ronald Swanson, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 137 days.

(21) Appl. No.: 13/794,887

(22) Filed: Mar. 12, 2013

(65) Prior Publication Data

US 2013/0295084 A1   Nov. 7, 2013

Related U.S. Application Data

(60) Provisional application No. 61/641,339, filed on May 2, 2012.

(51) Int. Cl.
*A61K 39/395* (2006.01)
*C07K 16/46* (2006.01)
*C07K 16/24* (2006.01)

(52) U.S. Cl.
CPC ............... *C07K 16/46* (2013.01); *C07K 16/468* (2013.01); *C07K 16/248* (2013.01); *C07K 2317/64* (2013.01); *C07K 2317/66* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,169,939 A | 12/1992 | Gefter et al. |
| 7,129,330 B1 | 10/2006 | Little et al. |
| 2005/0079170 A1 | 4/2005 | Le Gall et al. |
| 2007/0274985 A1 | 11/2007 | Dubel et al. |
| 2010/0254989 A1 | 10/2010 | Bossenmaier et al. |
| 2013/0058937 A1 | 3/2013 | Auer et al. |
| 2013/0060011 A1 | 3/2013 | Bruenker et al. |

FOREIGN PATENT DOCUMENTS

| | | | | |
|---|---|---|---|---|
| WO | WO 90/07861 A1 | 7/1990 | | |
| WO | WO 2006/093794 | * | 9/2006 | ............. C07K 16/00 |
| WO | WO 2007/024715 A2 | 3/2007 | | |
| WO | WO 2007/085814 A1 | 8/2007 | | |
| WO | WO 2009/018386 A1 | 2/2009 | | |
| WO | WO 2009/080251 A1 | 7/2009 | | |
| WO | WO 2009/080252 A1 | 7/2009 | | |
| WO | WO 2009/080253 A1 | 7/2009 | | |
| WO | WO 2009/080254 A1 | 7/2009 | | |

OTHER PUBLICATIONS

Bostrom, et al., "Variants of the Antibody Herceptin That Interact with HER2 and VEGF at the Antigen Binding Site," Science, 323: 1610-1614 (2009).

Brüsselbach, et al., "Enzyme recruitment and tumor cell killing in vitro by a secreted bispecific single-chain diabody," Tumor Targeting, 4: 115-123 (1999).

Carson, et al., "Human Lymphocyte Hybridomas and Monoclonal Antibodies," Advances in Immunology, 38: 275-311, Academic Press, Inc. (1986).

Paul J. Carter, "Potent antibody therapeutics by design," Nature Reviews, 6: 343-357 (2006).

Chan, et al., "Variable region domain exchange in human IgGs promotes antibody complex formation with accompanying structural changes and altered effector functions," Molecular Immunology, 41: 527-538 (2004).

Co, et al., "Chimeric and Humanized Antibodies with Specificity for the CD33 Antigen," The Journal of Immunology, 148: 1149-1154 (1992).

Randall T. Curnow, Clinical experience with CD64-directed immunotherapy. An Overview., Cancer Immunology and Immunotherapy, 45: 210-215 (1997).

Doppalapudi, et al., "Chemical generation of bispecific antibodies," Proceedings of the National Academy of Science USA, 107(52): 22611-22616 (2010).

Holliger, et al., "Diabodies: Small bivalent and bispecific antibody fragments," Proceedings of the National Academy of Science USA, 90: 6444-6448 (1993).

James, et al., "Monoclonal Antibodies, Their Production and Potential in Clinical Practice," Scottish Medical Journal, 29: 067-083 (1984).

Karacay, et al., "Experimental Pretargeting Studies of Cancer with a Humanized anti-CEA x Murine anti-[In-DTPA] Bispecific Antibody Construct and a $^{99m}$Tc-/$^{188}$Re-Labeled Peptide," Bioconjugate Chemistry, 11: 842-854 (2000).

Karpovsky, et al., "Production of Target-Specific Effector Cells Using Hetero-Cross-Linked Aggregates Containing Anti-Target Cell and Anti-Fcλ Receptor Antibodies," Journal of Experimental Medicine, 160: 1686-1701 (1984).

Köhler, et al., "Continuous cultures of fused cells secreting of predefined specificity," Nature, 256: 495-497 (1975).

Mack, et al., "A small bispecific antibody construct expressed as a functional single-chain molecule with high tumor cell cytotoxicity," Proceedings of the National Academy of Science USA, 92: 7021-7025 (1995).

Milstein, et al., "Hybrid hybridomas and their use in immunohistochemistry," Nature, 305: 537-540 (1983).

Sherie L. Morrison, "Transfectomas Provide Novel Chimeric Antibodies," Science, 229: 1202-1207 (1995).

Morrison, et al., "Variable Region Domain Exchange Influences the Functional Properties of IgG," Journal of Immunology, 160: 2802-2808 (1998).

Nettelbeck, et al., "Targeting of Adenovirus to Endothelial Cells by a Bispecific Single-Chain Diabody Directed against the Adenovirus Fiber Knob Domain and Human Endoglin (CD105)," Molecular Therapy, 3(6): 882-891 (2001).

(Continued)

*Primary Examiner* — Brad Duffy
*Assistant Examiner* — Nelson B Moseley, II
(74) *Attorney, Agent, or Firm* — Kirk Baumeister (57) ABSTRACT

The present invention relates to binding proteins having tethered light chains and methods of making and using them.

20 Claims, 1 Drawing Sheet

(56) References Cited

OTHER PUBLICATIONS

Queen, et al., "A humanized antibody that binds to the interleukin 2 receptor," Proceedings of the National Academy of Science USA, 86: 10029-10033 (1989).

Ridgeway, et al., "'Knobs-into-holes' engineering of antiby $C_H3$ domains for heavy chain heterodimerization," Protein Engineering, 9(7): 617-621 (1996).

Schaefer, et al., "Immunoglobulin Domain Crossover as a Genetic Approach for the Production of Bispecific IgG Antibodies," Proceedings of the National Academy of Science USA, 108(27): 11187-11192 (2011).

Simon, et al., "Antibody domain mutants demonstrate autonomy of the antigen binding site," The EMBO Journal, 9(4): 1051-1056 (1990).

Torisu-Itakura, et al., "Redirected Lysis of Human Melanoma Cells by a MSCP/CD3-bispecific BiTE Antibody That Engages Patient-derived T Cells," Journal of Immunotherapy, 34: 597-605 (2011).

PCT International Search Report dated Dec. 17, 2013.

* cited by examiner

SEQUENCE LISTING

```
<160> NUMBER OF SEQ ID NOS: 12

<210> SEQ ID NO 1
<211> LENGTH: 20
<212> TYPE: PRT
<213> ORGANISM: Artificial sequence
<220> FEATURE:
<223> OTHER INFORMATION: Synthetic linker

<400> SEQUENCE: 1

Gly Gly Gly Gly Ser Gly Gly Gly Gly Ser Gly Gly Gly Gly Ser Gly
1               5                   10                  15

Gly Gly Gly Ser
            20

<210> SEQ ID NO 2
<211> LENGTH: 30
<212> TYPE: PRT
<213> ORGANISM: Artificial Sequence
<220> FEATURE:
<223> OTHER INFORMATION: Synthetic linker

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 3
<211> LENGTH: 40
<212> TYPE: PRT
<213> ORGANISM: Artificial Sequence
<220> FEATURE:
<223> OTHER INFORMATION: Synthetic linker
```

```
<400> SEQUENCE: 3

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser
            35                  40

<210> SEQ ID NO 4
<211> LENGTH: 50
<212> TYPE: PRT
<213> ORGANISM: Artificial Sequence
<220> FEATURE:
<223> OTHER INFORMATION: Synthetic linkier

<400> SEQUENCE: 4

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser Gly Gly Gly Ser Gly Gly Gly
            35                  40                  45

Gly Ser
    50

<210> SEQ ID NO 5
<211> LENGTH: 107
<212> TYPE: PRT
<213> ORGANISM: Homo sapiens

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 106
<212> TYPE: PRT
<213> ORGANISM: Homo sapiens

<400> SEQUENCE: 6

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45
```

```
Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 326
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 9
<211> LENGTH: 327
<212> TYPE: PRT
<213> ORGANISM: Homo sapiens

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 10
<211> LENGTH: 184
<212> TYPE: PRT
<213> ORGANISM: Homo sapiens

<400> SEQUENCE: 10

```
Ala Ala Ile Gly Ser Cys Ser Lys Glu Tyr Arg Val Leu Leu Gly Gln
1               5                   10                  15

Leu Gln Lys Gln Thr Asp Leu Met Gln Asp Thr Ser Arg Leu Leu Asp
            20                  25                  30

Pro Tyr Ile Arg Ile Gln Gly Leu Asp Val Pro Lys Leu Arg Glu His
        35                  40                  45

Cys Arg Glu Arg Pro Gly Ala Phe Pro Ser Glu Thr Leu Arg Gly
    50                  55                  60

Leu Gly Arg Arg Gly Phe Leu Gln Thr Leu Asn Ala Thr Leu Gly Cys
65                  70                  75                  80

Val Leu His Arg Leu Ala Asp Leu Glu Gln Arg Leu Pro Lys Ala Gln
                85                  90                  95

Asp Leu Glu Arg Ser Gly Leu Asn Ile Glu Asp Leu Glu Lys Leu Gln
            100                 105                 110

Met Ala Arg Pro Asn Ile Leu Gly Leu Arg Asn Asn Ile Tyr Cys Met
        115                 120                 125

Ala Gln Leu Leu Asp Asn Ser Asp Thr Ala Glu Pro Thr Lys Ala Gly
    130                 135                 140

Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe
            180
```

<210> SEQ ID NO 11
<211> LENGTH: 263
<212> TYPE: PRT
<213> ORGANISM: Homo sapiens

<400> SEQUENCE: 11

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175
```

```
Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu Ile Phe Tyr Ile Ile
    210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
                260
```

<210> SEQ ID NO 12
<211> LENGTH: 266
<212> TYPE: PRT
<213> ORGANISM: Mus musculus

<400> SEQUENCE: 12

```
Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Phe Glu Gln Asp Gly Arg Lys Leu Asn
    115                 120                 125

Val Val Val Lys Asp Ser Leu Thr Leu Val Arg Lys Asn Gly Thr Phe
130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
    195                 200                 205

Ser Ser Thr Val Cys Thr Glu Gln Trp Lys Ser Phe Leu Gly Glu Thr
210                 215                 220

Leu Ile Ile Val Gly Ala Val Val Leu Leu Ala Thr Ile Phe Ile Ile
225                 230                 235                 240

Leu Leu Ser Ile Ser Leu Cys Lys Arg Arg Lys Asn Arg Ala Gly Gln
                245                 250                 255

Lys Gly Lys Asn Thr Pro Ser Arg Leu Ala
                260                 265
```

BINDING PROTEINS HAVING TETHERED LIGHT CHAINS

CROSS REFERENCE TO RELATED APPLICATIONS

This application claims the benefit of U.S. Provisional Application No. 61/641,339, filed 2 May 2012, the entire contents of which is incorporated herein by reference.

FIELD OF THE INVENTION

The present invention relates to binding proteins having tethered light chains and methods of making and using them.

BACKGROUND OF THE INVENTION

A number of human diseases are today treated by therapeutic monoclonal antibodies, for example humanized or fully human monoclonal antibodies. In 1975, Kohler and Milstein produced murine hybridomas that secreted monoclonal antibodies (mAbs) of defined specificity and ushered in the modern era of therapeutic mAbs utilizing these new hybridoma technologies (Kohler and Milstein, *Nature* 256: 495-97, 1975). However, major limitations of these early therapeutics included the lack of effector function, reduced serum half-life and the increased propensity to elicit an undesired immune response. Chimerization and humanization technologies helped to overcome these unwanted characteristics (Carson and Friemark, *Adv. Immunol.* 38:275-311, 1986; James et al., *Scottish Med. J.* 29: 67-83, 1984; Morrison, *Science* 229:1202-1207, 1985).

First generation bispecific antibodies (BsmAbs) that were produced by fusing two established hybridoma cell lines together to form a hybrid hybridoma or quadroma (Milstein and Cuello, *Nature* 305:537-540, 1983) or by chemical crosslinking two F(ab') fragments (Karpovsky et al., *J. Exp. Medicine* 160: 1686-1701, 1984) allowed simultaneous modulation of multiple targets. Although these studies highlighted the therapeutic potential of BsmAbs, these approaches, in addition to adverse in vivo responses to murine antibody fragments, presented logistical problems with respect to producing large, homogenous lots of purified antibodies. For example, random association of heavy and light chains secreted by the hybrid hybridomas results in production of 10 different antibody species from which the desired bispecific molecule should be isolated.

The first humanized BsmAb, MDX-447, (Curnow, *Cancer Immunol. Immunother.* 45:210-215, 1997) was generated by CDR-grafting followed by chemical coupling of the two Fab' domains to create a bispecific F(ab')2 molecule. However, the process of reduction, oxidation and subsequent purification underscores the key hurdle in generating highly pure BsmAb molecules from the employment of these methods. Isolation and purification of the heterodimeric species from a homodimeric species is not possible at production scale (Karacay et al., *Bioconjugate Chem.* 11:842-854, 2000).

Additional BsmAb platforms have been developed including diabodies (Holliger et al., *Proc. Natl. Acad. Sci.* 90: 6444-6448, 1993), single-chain diabodies (Brusselbach et al., *Tumor Targeting* 4:115-123, 1999; Nettlebeck et al., *Molecular Therapy* 3:882-891, 2001), tandem single-chain variable fragments (scFv) (Bi-specific T-cell engagers (BiTEs)) (Mack et al., *Proc. Natl. Acad. Sci.* 92:7021-7025, 1995.), knob and hole mAbs (Ridgeway et al., *Protein Engineering* 9:617-621, 1996.), and dual variable domain antibodies (WO2007/024715).

There is a need in the art for improved binding proteins capable of binding at least one target and providing ease of manufacturing and reduced cost of goods.

SUMMARY OF THE INVENTION

One aspect of the invention is a binding protein comprising a tethered light chain, a first heavy chain and a second heavy chain that specifically binds at least one antigen.

Another aspect of the invention is a binding protein comprising a tethered light chain, a first heavy chain and a second heavy chain produced according to a method comprising culturing a host cell under conditions sufficient to produce the binding protein, wherein the host cell comprises a vector, the vector comprising a nucleic acid encoding the tethered light chain, the first heavy chain and the second heavy chain.

Another aspect of the invention is an isolated polynucleotide encoding the binding protein of the invention.

Another aspect of the invention is an isolated vector comprising an isolated polynucleotide encoding the binding protein of the invention.

Another aspect of the invention is a host cell comprising a vector of the invention.

Another aspect of the invention is methods of making a binding protein of the invention comprising culturing a host cell of the invention under conditions sufficient to produce the binding protein.

Another aspect of the invention is a method of making a bispecific binding protein that binds a first antigen and a second antigen comprising an inside-out tethered light chain, a first inside-out heavy chain and a second inside-out heavy chain, comprising providing an antibody that binds the first antigen having a first light chain comprising a first light chain variable region (VL1) and a first light chain constant region (CL1), and a first heavy chain comprising a first heavy chain variable region (VH1) and a first heavy chain constant region (CH1); providing an antibody that binds the second antigen having a second light chain comprising a second light chain variable region (VL2) and a second light chain constant region (CL2), and a second heavy chain comprising a second heavy chain variable region (VH2) and a second heavy chain constant region (VC2); providing a linker; operably linking VH1-CL1-linker-VH2-CL2 from the N-terminus to the C-terminus to generate the inside-out tethered light chain; operably linking VL1-CH1 from the N-terminus to the C-terminus to generate the first inside-out heavy chain; operably linking VL2-CH2 from the N-terminus to the C-terminus to generate the second inside-out heavy chain; expressing the inside-out tethered light chain, the first inside-out heavy chain and the second inside-out heavy chain; and recovering the bispecfic binding protein.

Another aspect of the invention is a bispecific binding protein produced by methods of the invention.

Another aspect of the invention is a pharmaceutical composition comprising the binding protein of the invention and a pharmaceutically acceptable carrier.

DETAILED DESCRIPTION OF THE INVENTION

The term "binding protein" as used herein means a protein specifically binding one or more antigens having one tethered immunoglobulin light chain and two immunoglobulin heavy chains, or fragments thereof. Structures of immunoglobulin light and heavy chains are well known.

"Inside-out light chain" as used herein refers to a synthetic immunoglobulin light chain having a variable region derived from a heavy chain variable region operably linked to a light chain constant region. "Inside-out heavy chain" as used herein refers to a synthetic immunoglobulin heavy chain having a variable region derived from a light chain variable region operably linked to a heavy chain constant region. "Inside-out tethered light chain" as used herein refers to a tethered light chain having a first inside-out light chain operably linked from its C-terminus to a N-terminus of a second inside-out light chain via a polypeptide linker. Typically, "inside-out" light and heavy chains are generated by V region exchange of an existing antibody specifically binding an antigen (Simon and Rajewsky, *EMBO J.* 9:1051-1056, 1990).

The term "tethered light chain" as used herein means a synthetic antibody chain having a first light chain operably linked from its C-terminus to an N-terminus of a second light chain via a polypeptide linker. The first and the second light chains may be naturally occurring or synthetic.

The term "variable region" as used herein means an antibody light chain variable region (VL) or antibody heavy chain variable region (VH) that include amino acid sequences of antigen binding sites (for example CDR1, CDR2, CDR3) and frameworks (for example FR1, FR2, FR3, FR4). The light chain variable region (VL) can be kappa (κ) or lambda (λ) and is encoded by antibody IGVK or IGVL and IGJK or IGJL genes, and the heavy chain variable region (VH) is encoded by antibody IGVH, IGDH, and IGJH genes. Genomic organization of the human heavy and light chain gene loci, antibody gene structures, gene rearrangements and sequences are well known in the art.

An antibody variable region consists of a "framework" region interrupted by three "antigen binding sites." The antigen-binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat, *J. Exp. Med.* 132:211-250, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, *Mol. Biol.* 196:901-917, 1987). Other terms include "IMGT-CDRs" (Lefranc et al., *Dev. Comparat. Immunol.* 27:55-77, 2003) and "Specificity Determining Residue Usage" (SDRU) (Almagro, *Mol. Recognit.* 17:132-143, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., *Dev. Comparat. Immunol.* 27:55-77, 2003.

"Framework" or "framework sequences" are the remaining sequences of a variable region other than those defined to be antigen binding site. The framework is typically divided into four regions, FR1, FR2, FR3, and FR4, which form a scaffold for the three antigen binding sites in each variable region. Because the antigen binding site can be defined by various terms as described above, the exact amino acid sequence of a framework depends on how the antigen-binding site was defined.

The term "constant region" as used herein means an antibody light chain constant region (CL) or an antibody heavy chain constant region (CH). Depending on the amino acid sequence of the constant region of heavy chains, antibodies can be assigned to five major classes, namely IgA, IgD, IgE, IgG and IgM. IgA and IgG are further sub-classified as the isotypes $IgA_1$, $IgA_2$, $IgG_1$, $IgG_2$, $IgG_3$ and $IgG_4$. Sequences of antibody constant regions are well known.

The term "bispecific" as used herein means a binding protein that is engineered to comprise two antigen binding sites that each specifically binds a different antigen or a different epitope.

The term "monospecific" as used herein means that a binding protein has one or more antigen binding sites each of which bind to the same antigen or epitope.

The term "linker" or "polypeptide linker" as used herein means a polypeptide linker comprising two or more amino acids residues joined by peptide bonds. Such linker polypeptides are well known in the art (see e.g., Holliger, et al., *Proc. Natl. Acad. Sci. USA* 90:6444-6448, 1993; Poljak, et al., *Structure* 2:1121-1123, 1994). Exemplary linkers contain glycine (G) and serine (S), for example $(G_xS)_y$ (x=3-4, y=4-10), such as $(G_4S)_6$ (SEQ ID NO: 2). Any linker known in the art may be optionally selected and used in the present invention as long as it can operably link the two light chains together to generate a tethered light chain. The peptide linker may be about 2-70 amino acids, about 5-50 amino acids, about 10-40 amino acids, or about 20 amino acids in length.

The term "operably linked" as used herein refers to a positioning of components such that they function in their intended manner. The length of the linker may be experimentally determined by testing a series of tethered light chains operably linked by linkers of different lengths expressed with heavy chains for the ability of the formed binding proteins to bind at least one predetermined antigen.

The term "specifically binds" or "specifically binding" as used herein refers to the binding of a binding protein to a predetermined antigen. The affinity of the binding is defined in terms of a dissociation constant ($K_D$). The binding protein specifically binds an antigen when the $K_D$ is less than about $10^{-7}$ M, such as about $10^{-8}$ M or less, such as about $10^{-9}$ M or less, about $10^{-10}$ M or less; about $10^{-11}$ M or less, about $10^{-12}$ M or less, or even less, and binds to the predetermined antigen with an affinity corresponding to a $K_D$ that is at least ten-fold lower than its affinity for binding to a non-specific antigen (such as BSA or casein), such as at least 100 fold lower, for instance at least 1,000 fold lower, such as at least 10,000 fold lower. A bispecific binding protein specifically binds two different antigens or epitopes. Affinity can be measured using well know methods, for example in an in vitro assay using plasmon resonance (BIAcore, GE-Healthcare Uppsala, Sweden).

The term "antigen" as used herein refers to an epitope that is recognized by the binding protein of the invention. Antigens may be portions of a protein, a peptide, carbohydrate, lipid, and the like.

The term "$K_D$", as used herein, refers to the dissociation constant of a particular binding protein-antigen interaction as is known in the art.

The term "$K_{on}$", as used herein, refers to the on rate constant for association of a binding protein to the antigen to form the antibody/antigen complex as is known in the art.

The term "$K_{off}$", as used herein, refers to the off rate constant for dissociation of a binding protein from the binding protein/antigen complex as is known in the art.

The term "epitope" as used herein means a portion of an antigen to which a binding protein specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space.

The term "substantially identical" as used herein means that the two polypeptide sequences being compared are identical or have substitutions that do not result in alterations in the binding properties of the polypeptide. Typically, this involves one or more amino acid substitutions with an amino acid having similar charge, hydrophobic, or stereochemical characteristics, or with alanine. Function-retaining amino acid substitutions can be determined and tested by those skilled in the art. Exemplary amino acid substitutions are shown in Table 1.

The present invention provides binding proteins specifically binding at least one antigen and thus can be widely used in therapeutic and diagnostic applications. The invention is based on a discovery that engineered tethered light chains can be coexpressed with heavy chains to form functional binding proteins binding to at least one predetermined antigen with high affinity. The binding proteins of the invention can be engineered to be bispecfic, facilitating expression and purification protocols and improving yields while retaining Fc effector functions.

The present invention provides polynucleotides encoding the binding proteins of the invention or complementary nucleic acids thereof, vectors, host cells, and methods of making and using them.

TABLE 1

| Original residue | Exemplary substitutions | More Conservative substitutions |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Binding Proteins Comprising Tethered Light Chains

Figure 1:
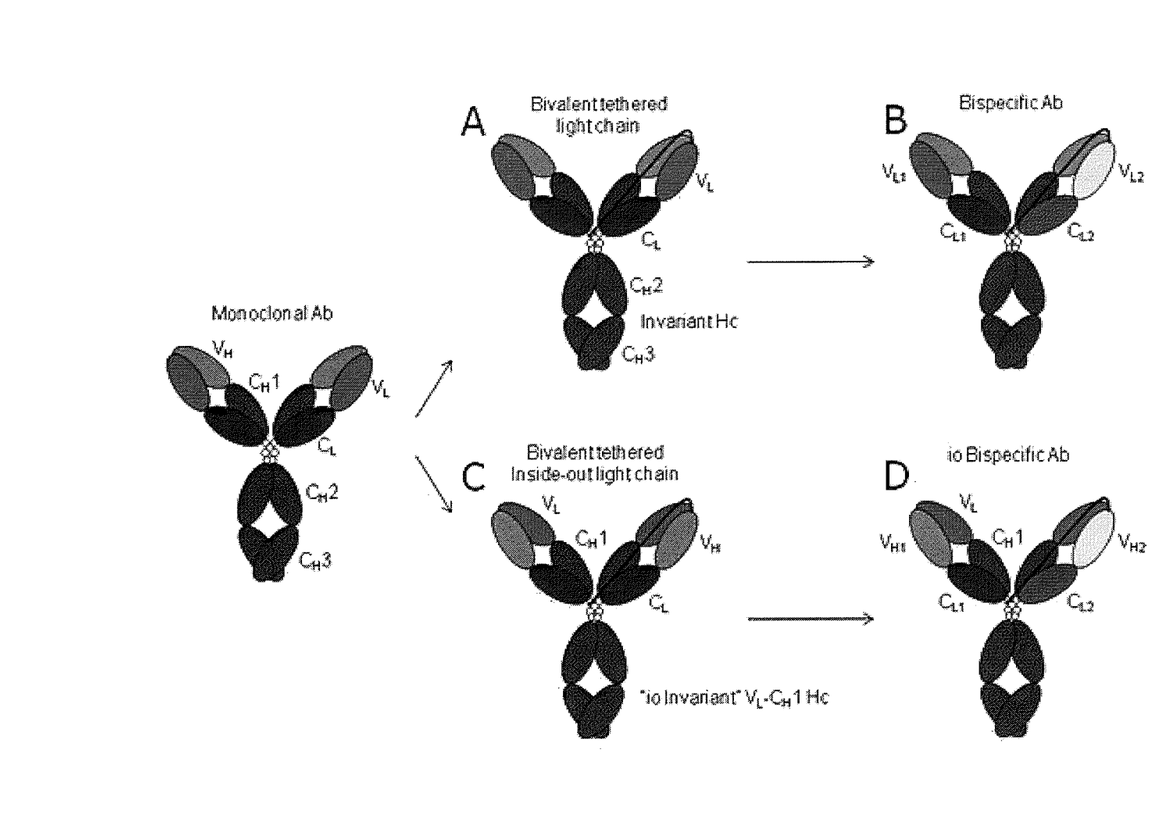
FIG. 1 shows design of binding proteins having tethered light chains. A) bivalent monospecific tethered light chain containing binding protein; B) bispecific, tethered light chain containing binding protein; C) bivalent, inside-out tethered light chain containing binding protein; D) bispecific, inside-out tethered light chain containing binding protein. Io: inside-out

FIG. 1 shows various designs of binding proteins comprising tethered light chains.

Antibody domains are referred in the specification as:
 i. VL1: a first light chain variable region
 ii. VL2: a second light chain variable region;
 iii. CL: a light chain constant region;
 iv. VH1: a first heavy chain variable region;
 v. VH2: a second heavy chain variable region;
 vi. CH: a heavy chain constant region.

Linker as referred to is a polypeptide linker.

Antigen binding sites in the binding proteins of the invention are formed by VL1/VH1 and VL2/VH2 pairs. The two pairs may bind the same or different antigen, resulting in monospecific or bispecific binding proteins.

In one embodiment, the binding protein of the invention comprises a tethered light chain, a first heavy chain and a second heavy chain, wherein the binding protein specifically binds at least one antigen.

In another embodiment, the binding protein comprises a tethered light chain comprising VL1-CL-linker-VL2-CL, a first heavy chain comprising VH1-CH, and a second heavy chain comprising VH2-CH.

In another embodiment, the binding protein of the invention comprises an inside-out tethered light chain, a first inside-out heavy chain and a second inside-out heavy chain, wherein the binding protein specifically binds at least one antigen.

In another embodiment, the binding protein comprises an inside-out tethered light chain comprising VH1-CL-linker-VH2-CL, a first inside-out heavy chain comprising VL1-CH, and a second inside-out heavy chain comprising VL2-CH.

The inside-out tethered light chains and inside-out heavy chains of the binding proteins of the invention can be generated using variable domain exchange wherein variable domains typically originate from an antibody specifically binding an antigen (see Simon and Rajewsky, *EMBO J* 9:1051-1056, 1990).

In another embodiment, the binding protein of the invention comprises an inside-out tethered light chain comprising VH1-CL-linker-VH2-CL, a first inside-out heavy chain comprising VL1-CH, and a second inside-out heavy chain comprising VL2-CH, wherein the binding protein is bispecific.

The inside-out tethered light chains and the inside-out heavy chains of the bispecific binding proteins of the invention can be generated using variable domain exchange wherein variable domains typically originate from two antibodies each specifically binding a different antigen (see Simon and Rajewsky, *EMBO J* 9:1051-1056, 1990). Generation of bispecific binding molecules using variable domain exchange to create inside-out tethered light chains presents a new approach to generate a high specificity light chain molecules where different antigen specificities can be added in tandem and expressed as a single recombinant protein. In an exemplary bispecific binding protein, the VL1 and the VH1 are derived from an antibody specifically binding a first antigen and the VL2 and the VH2 are derived from an antibody specifically binding a second antigen. In another exemplary bispecific binding protein, the inside-out tethered light chain comprises VH1 and VH2 derived from the first and the second antibody each specifically binding a different antigen, whereas the VL1 and the VL2 domains in the first and the second inside-out heavy chain have identical or substantially identical amino acid sequences, i.e. the VL1 and the VL2 are derived from the first antibody specifically binding the first antigen. Many antibodies, for example Herceptin® (trastuzumab) (Bostrom et al., *Science* 323:1610-1614, 2009) bind antigens predominantly through their heavy chains. Creating tethered inside-out light chains allows the heavy chain variable region specificity of the first antibody specifically binding a first antigen and the second antibody specifically binding a second antigen to be transferred into the inside-out tethered light chain, and allows expression and purification of bispecific binding proteins of the invention in a similar manner to conventional antibodies as only one inside-out heavy chain is required for co-expression and retainment of binding specificity.

Exemplary linkers that can be used to tether two light chains are linkers containing poly-glycine or glycine and serine. The use of naturally occurring as well as artificial peptide linkers to connect polypeptides into novel linked fusion polypeptides is well known in the art (Hallewell et al., *J Biol Chem* 264:5260-5268, 1989; Alfthan et al., *Protein Eng.* 8:725-731, 1995; Robinson & Sauer, *Biochemistry* 35:109-116, 1996; U.S. Pat. No. 5,856,456). Exemplary linkers are $(G_4S)_4$ (SEQ ID NO: 1), $(G_4S)_6$ (SEQ ID NO: 2), $(G_4S)_8$ (SEQ ID NO: 3), and $(G_4S)_{10}$ (SEQ ID NO: 4).

Variable regions of the binding proteins of the invention may be any mammalian or rodent variable region, such as human, rabbit, mouse, or rat, from chimeric, humanized, human-adapted or human variable regions.

The tethered light chain constant regions (CL) may be any mammalian or rodent constant region, such as human, rabbit, mouse, or rat. Exemplary light chain constant regions are human Cκ (SEQ ID NO:5) and Cλ (SEQ ID NO:6).

Heavy chains in the exemplary binding proteins of the invention may be of the IgG, IgD, IgE, IgA or IgM isotypes. Exemplary heavy chain constant regions (CH) may be derived from any mammalian or rodent constant region, such as human, rabbit, mouse, or rat. For example, a useful human heavy chain constant region is of IgG1 (SEQ ID NO: 7), IgG2 (SEQ ID NO: 8) or IgG4 (SEQ ID NO: 9) type.

The binding proteins of the invention can be post-translationally modified by processes such as glycosylation, isomerization, deglycosylation or non-naturally occurring covalent modification such as the addition of polyethylene glycol (PEG) moieties (pegylation) and lipidation. Such modifications may occur in vivo or in vitro. For example, the binding proteins of the invention may be conjugated to polyethylene glycol (PEGylated) to improve their pharmacokinetic profiles. Conjugation can be carried out by techniques known to those skilled in the art. Conjugation of, for example, therapeutic antibodies with PEG has been shown to enhance pharmacodynamics while not interfering with function (Deckert et al., *Int. J. Cancer* 87:382-390, 2000; Knight et al., *Platelets* 15:409-418, 2004; Leong et al., *Cytokine* 16:106-119, 2001; Yang et al., *Protein Eng.* 16:761-770, 2003).

The binding proteins of the invention can be optimized for their Fc-mediated effector functions such as antibody-dependent cellular cytotoxicity (ADCC), antibody-dependent cell phagocytosis (ADCP), and/or complement-dependent cytotoxicity (CDC) by techniques known to those skilled in the art. "Fc" is a term well known and is defined on the basis of papain cleavage of antibodies. Suitable substitutions in heavy chain residues for Fc engineering are well known in the art (for review, see Strohl, *Curr Opin Biotechnol.* 20:685-91, 2009).

Methods of Making Binding Proteins of the Invention

The binding proteins of the invention can be generated by engineering using standard molecular biology techniques using existing antibodies binding a desired antigen as templates. PCR methods can be used followed by standard cloning to generate the tethered light chains and heavy chains. Nucleic acids encoding tethered light chains and heavy chains are inserted into the same or different expression vector and are operably linked to control sequences such as signal sequence, a promoter, an enhancer, and a transcription termination sequence (see Queen et al., *Proc. Natl. Acad. Sci.* USA 86, 10029-10032, 1989; WO 90/07861; Co et al., *J. Immunol.* 148, 1149, 1992).

One embodiment of the invention is a method of making a bispecific binding protein that binds a first antigen and a second antigen comprising an inside-out tethered light chain, a first inside-out heavy chain and a second inside-out heavy chain, comprising a) providing an antibody that binds the first antigen having a first light chain comprising a first light chain variable region (VL1) and a first light chain constant region (CL1), and a first heavy chain comprising a first heavy chain variable region (VH1) and a first heavy chain constant region (CH1);

b) providing an antibody that binds the second antigen having a second light chain comprising a second light chain variable region (VL2) and a second light chain constant region (CL2), and a second heavy chain comprising a second heavy chain variable region (VH2) and a second heavy chain constant region (VC2);

c) providing a linker;

d) operably linking VH1-CL1-linker-VH2-CL2 from the N-terminus to the C-terminus to generate the inside-out tethered light chain;

e) operably linking VL1-CH1 from the N-terminus to the C-terminus to generate the first inside-out heavy chain;

f) operably linking VL2-CH2 from the N-terminus to the C-terminus to generate the second inside-out heavy chain;

g) expressing the inside-out tethered light chain, the first inside-out heavy chain and the second inside-out heavy chain; and h) recovering the bispecfic binding protein.

Tethered light chain and heavy chain variable regions of binding proteins of the invention may be derived from antibodies made by the hybridoma method of Kohler et al., *Nature* 256:495-497, 1975. Variable regions derived from human-adapted mAbs having CDRs derived from a non-human donor immunoglobulin and frameworks derived from one or more human immunoglobulins can be prepared by techniques known to those skilled in the art such as that disclosed in U.S. Pat. No. 5,225,539. Human framework sequences useful for human-adaptation can be selected from relevant databases by those skilled in the art. Human-adapted mAbs can optionally be further modified by incorporating altered framework support residues to preserve binding affinity by techniques such as those disclosed in Queen et al., *Proc. Natl. Acad. Sci.* (*USA*) 86:10029-10032, 1989 and Hodgson et al., *Bio/Technology* 9:421, 1991.

Variable regions derived from fully human antibodies can be prepared from human immunoglobulin transgenic mice by techniques referenced in, e.g., Lonberg et al., *Nature* 368:856-859, 1994; Fishwild et al., *Nature Biotechnology* 14:845-851, 1996; and Mendez et al., *Nature Genetics* 15:146-156, 1997. Fully human antibodies can also be prepared and optimized from phage display libraries by techniques referenced in, e.g., Knappik et al., *J. Mol. Biol.* 296:57-86, 2000; and Krebs et al., *J. Immunol. Meth.* 254:67-84 2001; Shi et al., *J Mol Biol.* 397:385-96, 2010.

Variable regions of the binding proteins of the invention can also be derived from antibody libraries using ribosome display (Mattheakis et al., *Proc. Natl. Acad. Sci.* USA 91:9022-6, 1994) and bacterial displays (Chen and Georgiou, *Biotechnol Bioeng*, 79:496-503, 2002).

The binding proteins of the invention may be purified by standard methodologies used for purifying immunoglobulin molecules, for example, by chromatography (e.g., ion exchange, affinity, and sizing column chromatography). The binding proteins of the present invention or fragments thereof can be fused to heterologous polypeptide sequences described herein or otherwise known in the art, to facilitate purification.

The affinity of a binding protein of the invention for an antigen can be determined experimentally using any suitable method. (See, for example, Berzofsky, et al., "Antibody-Antigen Interactions," in *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular binding protein-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of binding protein and antigen, and a standardized buffer, such as the buffer described herein.

Polynucleotides, Vectors, and Host Cells

The invention provides for nucleic acids encoding the binding proteins of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions thereof. Certain exemplary polynucleotides are disclosed herein, however, other polynucleotides which, given the degeneracy of the genetic code or codon preferences in a given expression system, encode the binding proteins of the invention are also within the scope of the invention.

The polynucleotides of the invention may be produced by chemical synthesis such as solid phase polynucleotide synthesis on an automated polynucleotide synthesizer and assembled into complete single or double-stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, and the like. The polynucleotide sequence's may also comprise additional sequences encoding additional amino acids that encode for example a marker or a tag sequence such as a hexa-histidine or an HA tag to facilitate purification or detection of the protein, or a signal sequence.

An exemplary polynucleotide comprises sequences for a CMV promoter, a signal sequence, and sequences encoding an inside-out tethered light chain or an inside-out heavy chain of the binding protein of the invention, a SV40 polyadenlyation site, and a bacterial origin of replication (ori).

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising a vector of the invention. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44, or HEK93 cell lines.

Uses of Binding Proteins of the Invention.

The compositions of the binding proteins described herein and generated by any of the above described methods may be used to diagnose, monitor, modulate, treat, alleviate, help prevent the incidence of, or reduce the symptoms of human disease or specific pathologies in cells, tissues, organs, fluid, or, generally, a host. A binding protein engineered for a specific purpose may be used to treat an immune-mediated or immune-deficiency disease, a metabolic disease, a cardiovascular disorder or disease; a malignant disease; a neurologic disorder or disease; an infection such as a bacterial, viral or parasitic infection; or other known or specified related condition including swelling, pain, and tissue necrosis or fibrosis.

Such a method can comprise administering an effective amount of a composition or a pharmaceutical composition comprising at least one binding protein specifically binding an antigen to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

Pharmaceutical Compositions Comprising Binding Proteins of the Invention

For therapeutic use, the binding proteins specifically binding an antigen may be prepared as pharmaceutical compositions containing an effective amount of the binding protein as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the binding protein of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations, inclusive of other human proteins, for example, human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration for therapeutic use of the binding protein of the invention may be any suitable route that delivers the agent to the host, such as parenteral administration, for example, intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

While having described the invention in general terms, the embodiments of the invention will be further disclosed in the following examples that should not be construed as limiting the scope of the claims.

Materials and Methods

Cloning and Expression

Heavy and light chains were cloned using standard methods. To generate an inside-out tethered light chain, a heavy chain variable region of an antibody specifically binding an antigen was operably linked onto Igκ constant region. To generate an inside-out heavy chain, a light chain variable region of an antibody specifically binding an antigen was operably linked onto human IgG1 constant region. Tethered inside-out light chains were generated by operably linking two inside-out light chains via a (G$_4$S) linker of various lengths to generate a VH-Igκ-linker-VH-Igκ polypeptide.

Antibodies used as templates for VH and VL domains were anti-human oncostatin M antibodies OSMM55 and OSMM69 (described in U.S. Published Patent Appl. No. 2012-0093833 A1), anti-human tissue factor antibodies TF7M16 and TF7M58 (described in U.S. Published patent Appl. No. 2012-0237528 A1) and anti-mouse tissue factor antibody MTFM27.

HEK93-F cells were transiently transfected with the generated constructs using Freestyle™ Max transfection reagent (Invitrogen Cat #16447), and the expressed antibodies were purified from the media after 4 days of culture using protein A and Superdex 200 size exclusion columns. Fractions corresponding to the monomer peak were collected and pooled. The quality of the purified proteins was assessed by SDS-PAGE and analytical size exclusion HPLC (Dionex HPLC system). Purified proteins were stored at 4° C. until assays were performed.

Protein Purification

Purifications were performed using the AKTA FPLC chromatography systems. Cell supernatants from transiently transfected HEK293-F cells were harvested 4 days after transfection, clarified by centrifugation (30 min, 6000 rpm) and filtered (0.2 μm PES membrane, Corning, Acton, Mass.). Samples transfected at 1-2 L scale were concentrated 10-fold using a Centramate concentrator (Pall Corporation, Port Washington, N.Y.). The concentrated samples were then diluted with 10×PBS to a final concentration of 1×PBS, and again 0.2 μM filtered. Diluted supernatants were loaded onto an equilibrated (PBS, pH 7) HiTrap MabSelect Sure Protein A column (GE Healthcare, Waukesha, Wis.) at a relative concentration of ~10 mg protein per ml of resin. After loading, the column was washed with PBS, pH7 and protein eluted with 10 column volumes of 0.1 M Na-Acetate, pH 3.5. Protein fractions were neutralized by the addition of 1M tris-HCl, pH 8.0. Peak fractions were pooled, concentrated and loaded onto a Superdex 200 size exclusion column pre-equilibrated with PBS, pH 7.2. Fractions corresponding to the monomer peak were collected and pooled. The quality of the purified proteins was assessed by SDS-PAGE (FIG. 3) and analytical size exclusion HPLC (Dionex HPLC system). Purified proteins were stored at 4° C. until assays were performed.

Biacore Analysis

Affinity measurements using Surface Plasmon Resonance (SPR) were performed using a Biacore 3000 optical biosensor (Biacore). The collected data were processed using BIAevaluation software, version 3.2 (Biacore). Then kinetic analysis of the data was performed using 1:1 binding model with global fit. The result for each mAb was reported in the format of Ka (On-rate), Kd (Off-rate) and K$_D$ (affinity constant).

Anti-OSM Antibodies. Approximately 9,000 RU (response units)/well of anti-Human IgG Fc (Jackson cat #109-005-098) were immobilized to the carboxymethylated dextran surface of a CM-5 chip (Biacore, Cat #BR-1000-14) according to the manufacturer instructions. The kinetic experiments were performed at 25° C. in running buffer (DPBS+0.005% P20+3 mM EDTA+100 μg/ml BSA). Serial dilutions of human OSM ECD (SEQ ID NO:10) from 25 nM to 0.391 nM were prepared in running buffer. About 50-70 RU of mAb were captured on flow cell 2 to 4 of the sensor chip. Flow cell 1 was used as reference surface. Capture of mAb was followed by a three minute injection (association phase) of antigen at 50 μL/min, followed by 20 or 120 minutes of buffer flow (dissociation phase). The chip surface was regenerated by two pulses of 18 second injections of 100 mM H$_3$PO$_4$ (Sigma, Cat #7961) at 50 μL/min.

Anti-tissue factor antibodies. Approximately 19,000 RU (response units) of anti-IgG Fc antibodies (mixture of anti-Mouse (Jackson cat #315-005-046) and anti-Human (Jackson cat #109-005-098)) were immobilized to the carboxymethylated dextran surface of a CM-5 chip (Biacore, Cat #BR-1000-14). The kinetic experiments were performed at 37° C. in running buffer (DPBS+0.005% P20+3 mM EDTA+100 μg/ml BSA). Serial dilutions of human TF ECD (SEQ ID NO: 11) and murine TF ECD (SEQ ID NO: 12) from 900 nM to 0.412 nM were prepared in running buffer. About 200-300 RU of mAb were captured on flow cell 2 to 4 of the sensor chip. Flow cell 1 was used as reference surface. Capture of mAb was followed by a three minute injection (association phase) of antigen at 50 μL/min, followed by 10 minutes of buffer flow (dissociation phase). The chip surface was regenerated as described above.

Bispecific functions of antibodies were tested using serial injection of 300 nM human TF ECD and mouse TF ECD for 5 minutes each. The chip surface was regenerated as described above. Alternatively, assays were performed using a Streptavidin sensor (Biacore, Cat #BR-1000-32) onto which about 900 RU of biotinylated human TF ECD was captured. Capture of the antigen was followed by a five minutes injection of mAb (300 nM) and a five minutes injection of mouse TF ECD. The chip surface was regenerated as described above.

For affinity measurements, a mature human human oncostatin M (hOSM) polypeptide (SEQ ID NO: 10), a human tissue factor (hTF) polypeptide (SEQ ID NO: 11) or a mouse tissue factor (mTF) polypeptide (SEQ ID NO: 12) were used.

Example 1

Tethered Light Chain Binding Proteins

Two OSML186 light chains derived from an anti-oncostatin M antibody OSMM55 were tethered together via an extended, unstructured linker to be co-expressed and assembled with a heavy chain OSMH14 derived from the same antibody to form functional binding proteins. Similarly, two OSML178 light chains from an anti-oncostatin M antibody OSMM69 were tethered together and co-expressed with a heavy chain OSMH17 derived from the same antibody). Four different lengths of linkers were tested for each tethered light chain: $(G_4S)_4$ (SEQ ID NO: 1), $(G_4S)_6$ (SEQ ID NO: 2), $(G_4S)_8$ (SEQ ID NO: 3), and $(G_4S)_{10}$ (SEQ ID NO: 4), for their ability to promote optimal antibody assembly (lack of higher order "polymers"), binding and function as compared to parent antibodies with untethered light chains. Table 2 shows the binding proteins made and their light and heavy chain origins. The tethered light chains were of human Igκ and the heavy chains of human IgG1 type. The resulting binding proteins were purified and analyzed using SDS-PAGE and their binding affinities evaluated using Biacore.

TABLE 2

| Antibody/binding protein ID | Lc Type | VL peptide ID | Lc Linker | Hc Type | VH peptide ID |
|---|---|---|---|---|---|
| OSMM55 | parent | OSML186VL | | parent | OSMH14VH |
| OSMM173 | TLc | OSML186VL | $(G_4S)_4$ | parent | OSMH14VH |
| OSMM174 | TLc | OSML186VL | $(G_4S)_6$ | parent | OSMH14VH |
| OSMM176 | TLc | OSML186VL | $(G_4S)_8$ | parent | OSMH14VH |
| OSMM178 | TLc | OSML186VL | $(G_4S)_{10}$ | parent | OSMH14VH |
| OSMM69 | parent | OSML178VL | | parent | OSMH17VH |
| OSMM171 | TLc | OSML178VL | $(G_4S)_4$ | parent | OSMH17VH |
| OSMM172 | TLc | OSML178VL | $(G_4S)_6$ | parent | OSMH17VH |
| OSMM175 | TLc | OSML178VL | $(G_4S)_8$ | parent | OSMH17VH |
| OSMM177 | TLc | OSML178VL | $(G_4S)_{10}$ | parent | OSMH17VH |

Lc = Light chain
Hc = heavy chain
TLc = tethered light chain

The majority of the expressed tethered light chain binding proteins specifically binding OSM were in monomeric form. Linker length played into the propensity to form monomers over oligomers, where the tethered light chain with the $(G_4S)_6$ linker (SEQ ID NO: 2) resulted in the highest degree of monomeric monoclonal antibody. Tethered light chain OSM binding proteins retained similar affinities when compared to the antibodies from which the variable regions were derived from (Table 3).

TABLE 3

| Antibody/binding protein ID | Ka(1/Ms) | kd(1/s) | $K_D$(M) |
|---|---|---|---|
| OSMM55 | 6.16E+05 | 4.35E−06 | 7.06E−12 |
| OSMM173 | 5.60E+05 | 7.98E−06 | 1.43E−11 |

TABLE 3-continued

| Antibody/binding protein ID | Ka(1/Ms) | kd(1/s) | $K_D$(M) |
|---|---|---|---|
| OSMM174 | 5.19E+05 | 6.21E−06 | 1.20E−11 |
| OSMM176 | 4.93E+05 | 7.92E−06 | 1.61E−11 |
| OSMM178 | 4.18E+05 | 7.35E−06 | 1.76E−11 |
| OSMM69 | 6.69E+05 | 5.72E−06 | 8.54E−12 |
| OSMM171 | 6.36E+05 | 1.08E−05 | 1.70E−11 |
| OSMM172 | 5.33E+05 | 9.64E−06 | 1.81E−11 |
| OSMM175 | 5.93E+05 | 1.41E−05 | 2.37E−11 |
| OSMM177 | 5.27E+05 | 1.37E−05 | 2.59E−11 |

Example 2

Inside-Out and Inside-Out Tethered Light Chain Containing Binding Proteins

Inside-out light and heavy chains and inside-out tethered light chains were generated to evaluate their assembly into functional binding proteins and retention of their characteristics when compared to parent antibodies from which the variable regions originated from.

Inside-out antibodies were generated by V region exchange e.g exchange of VL and VH regions between the heavy and the light chain of a parental antibody.

For example, binding protein BISM7 was generated by replacing the VH region of the parental antibody heavy chain (TF7H16VH) with the VL region of the parental antibody light chain (TF7L2VL) to generate an inside-out heavy chain, and the VL region of the parental antibody light chain (TF7L2VL) was replaced with the VH region of the parental antibody (TF7H16VH) to generate inside-out light chains.

The tethered inside-out light chains were generated by operably linking two identical inside-out light chains via a $(G_4S)_6$ linker (SEQ ID NO: 2). The generated inside-out light chains or inside-out tethered light chains and inside-out heavy chains were co-expressed as pairs shown in Table 4, and the affinity of the purified binding proteins for human tissue factor (hTF) was measured using Biacore (Table 5). Both binding proteins with inside-out chains and inside-out tethered light chains expressed well, were isolated in a monomeric form and retained similar affinities when compared to parent antibodies,

TABLE 4

| Antibody/binding protein ID | Lc Type | VL peptide ID | Lc Linker | Hc Type | VH peptide ID |
|---|---|---|---|---|---|
| TF7M16 | parent | TF7L2VL | | parent | TF7H16VH |
| BISM7 | ioLc | TF7H16VH | $(G_4S)_6$ | ioHc | TF7L2VL |
| BISM9 | ioTLc | TF7H16VH | $(G_4S)_6$ | ioHc | TF7L2VL |
| TF7M58 | parent | TF7L2VL | | parent | TF7H22VH |
| BISM6 | ioLc | TF7H22VH | $(G_4S)_6$ | ioHc | TF7L2VL |
| BISM8 | ioTLc | TF7H22VH | $(G_4S)_6$ | ioHc | TF7L2VL |
| MTFM27 | parent | TF7L2VL | | parent | MTFH81VH |
| TF7M1666 | ioLc | MTFH81VH | $(G_4S)_6$ | ioHc | TF7L2VL |
| TF7M1667 | ioTLc | MTFH81VH | $(G_4S)_6$ | ioHc | TF7L2VL |
| TF7M1668 | biioTLc | TF7H22VH/ MTFH81VH | $(G_4S)_6$ | ioHc | TF7L2VL/ TF7L2VL |

Lc = light chain
Hc = heavy chain
TLc = tethered light chain
ioLc = inside out light chain
ioTLc = inside out tethered light chain
ioHc = inside out heavy chain
biioTLc = bispecific inside out tethered light chain
$(G_4S)_6$: SEQ ID NO: 2

TABLE 5

| Antibody | Ka(1/Ms) | kd(1/s) | $K_D$(M) |
|---|---|---|---|
| TF7M16 | 2.83E+05 | 7.87E-05 | 2.78E-10 |
| BISM7 | 2.76E+05 | 7.18E-05 | 2.60E-10 |
| BISM9 | 2.63E+05 | 3.17E-05 | 1.21E-09 |
| TF7M58 | 2.69E+05 | 7.43E-05 | 2.76E-10 |
| BISM6 | 2.78E+05 | 6.58E-05 | 2.37E-10 |
| BISM8 | 2.57E+05 | 1.00E-04 | 3.91E-10 |
| MTFM27* | | | |
| TF7M1666* | 4.88E+04 | 2.99E-04 | 6.12E-09 |
| TF7M1666 | | | NB |
| TF7M1667* | 4.58E+04 | 3.51E-04 | 7.66E-09 |
| TF7M1667 | | | NB |
| TF7M1668* | 5.66E+04 | 4.00E-04 | 7.06E-09 |
| TF7M1668 | 1.60E+05 | 9.02E-05 | 5.06E-10 |

*Binding against mouse tissue factor.
NB = no binding

Example 3

Bispecific Inside-Out Tethered Light Chain Binding Proteins

Bispecific binding proteins were generated by co-expressing a tethered inside-out light chain having two inside-out variable regions with different antigen specificity with an inside-out heavy chain. Anti-mouse tissue factor antibody MTFM27 specifically binds mouse tissue factor but does not cross-react with human ortholog, and an anti-human TF antibody TF7M58 specifically binds human TF but shows no binding to mouse TF. A tethered inside-out bispecific light chain was generated by operably linking MTFM27 VH domain to human Cκ and TF7M58 VH domain to human Cκ, and the two inside-out light chains were operably linked using a $(G_4S)_6$ linker Parental antibodies MTFM27 and TF7M58 share an identical light chain (TF7L2), and thus only one inside-out heavy chain was generated by joining the VL of antibody TF7M58 to human IgG1 constant region. The generated light and heavy chains were co-expressed, and the resulting bispecific binding protein (TF7M1668, Table 4) were analyzed for their binding affinities to human and mouse tissue factor using Biacore. Table 5 shows affinity of the binding protein to human and mouse TF.

We claim:

1. A binding protein comprising an inside-out tethered light chain, a first inside-out heavy chain and a second inside-out heavy chain that specifically binds at least one antigen, wherein the inside-out tethered light chain comprises VH1-CL-linker-VH2-CL, the first inside-out tethered heavy chain comprises VL1-CH, and the second inside-out tethered heavy chain comprises VL2-CH, wherein
   i) VL1 is a first light chain variable region;
   ii) VL2 is a second light chain variable region;
   iii) CL is a light chain constant region;
   iv) VH1 is a first heavy chain variable region;
   v) VH2 is a second heavy chain variable region;
   vi) CH is a heavy chain constant region comprising a $C_H1$ domain, hinge, a $C_H2$ domain, and $C_H3$ domain; and
   vii) linker is a polypeptide linker.

2. The binding protein of claim 1, wherein the VL1 and the VL2 comprise identical or substantially identical amino acid sequences.

3. The binding protein of claim 1, which is bispecific.

4. The binding protein of claim 1, wherein the VL1, the VL2, the VH1 and the VH2 comprise human, humanized, human-adapted or murine polypeptide sequences.

5. The binding protein of claim 1, wherein the CL is of kappa (κ) or lambda (λ) type and the CH is of IgG1, IgG2, IgG3, or IgG4 type.

6. The binding protein of claim 1, wherein the CL and CH are of human origin.

7. The binding protein of claim 1, wherein the linker is about 5-50 amino acids long.

8. The binding protein of claim 7, wherein the linker is $(G_4S)_4$ (SEQ ID NO: 1), $(G_4S)_6$ (SEQ ID NO: 2), $(G_4S)_8$ (SEQ ID NO: 3) or $(G_4S)_{10}$ (SEQ ID NO: 4).

9. The binding protein of claim 1, wherein the binding protein binds at least one antigen with a dissociation constant $(K_D)$ of at most about $10^{-9}$ M, at most about $10^{-10}$ M, at most about $10^{-11}$ M, at most about $10^{-12}$ M, or at most about $10^{-13}$ M.

10. The binding protein of claim 1, wherein the binding protein binds at least one antigen with an on rate constant $(K_{on})$ of at least about $10^4$ $M^{-1}$ $s^{-1}$, at least about $10^5$ $M^{-1}s^{-1}$, or at least about $10^4$ $M^{-1}s^{-1}$.

11. The binding protein of claim 1, wherein the binding protein binds at least one antigen with an off rate constant $(K_{off})$ of at most about $10^4$ $s^{-1}$, at most about $10^{-5}$ $s^{-1}$, or at most about $10^{-6}$ $s^{-1}$.

12. A binding protein of claim 1 produced according to a method comprising culturing a host cell under conditions sufficient to produce the binding protein, wherein the host cell comprises at least one vector, the at least one vector comprising a nucleic acid encoding the inside-out tethered light chain, the first inside-out heavy chain and the second inside-out heavy chain.

13. An isolated polynucleotide encoding the binding protein of claim 1.

14. A vector comprising an isolated polynucleotide of claim 13.

15. A host cell comprising a vector of claim 14.

16. A method of making the binding protein of claim 1 comprising culturing the host cell of claim 17 under conditions sufficient to produce the binding protein.

17. A method of making a bispecific binding protein that binds a first antigen and a second antigen comprising an inside-out tethered light chain, a first inside-out heavy chain and a second inside-out heavy chain, comprising
   a) providing an antibody that binds the first antigen having a first light chain comprising a first light chain variable region (VL1) and a first light chain constant region (CL1), and a first heavy chain comprising a first heavy chain variable region (VH1) and a first heavy chain constant region (CH1), wherein CH1 comprises a $C_H1$ domain, hinge, $C_H2$ domain, and a $C_H3$ domain;
   b) providing an antibody that binds the second antigen having a second light chain comprising a second light chain variable region (VL2) and a second light chain constant region (CL2), and a second heavy chain comprising a second heavy chain variable region (VH2) and a second heavy chain constant region (CH2), wherein CH2 comprises a $C_H1$ domain, hinge, a $C_H2$ domain, and a $C_H3$ domain;
   c) providing a linker;
   d) operably linking VH1-CL1-linker-VH2-CL2 from the N-terminus to the C-terminus to generate the inside-out tethered light chain;
   e) operably linking VL1-CH1 from the N-terminus to the C-terminus to generate the first inside-out heavy chain;
   f) operably linking VL2-CH2 from the N-terminus to the C-terminus to generate the second inside-out heavy chain;
   g) expressing the inside-out tethered light chain, the first inside-out heavy chain and the second inside-out heavy chain; and
   h) recovering the bispecfic binding protein.

18. The method of claim 17, wherein the VL1 and the VL2 comprise identical or substantially identical amino acid sequences.

19. A bispecific binding protein produced by a method of claim 17.

20. A pharmaceutical composition comprising the binding protein of claim 1 and a pharmaceutically acceptable carrier.

* * * * *